(12) United States Patent
Ding et al.

(10) Patent No.: US 7,457,686 B2
(45) Date of Patent: Nov. 25, 2008

(54) ROBOTIC ARM ALIGNMENT

(75) Inventors: Zhong Ding, Pittsford, NY (US); Ed Graham, Penfield, NY (US)

(73) Assignee: Ortho_Clinical Diagnostics, Inc., Rochester, NY (US)

( * ) Notice: Subject to any disclaimer, the term of this patent is extended or adjusted under 35 U.S.C. 154(b) by 32 days.

(21) Appl. No.: 11/685,854

(22) Filed: Mar. 14, 2007

(65) Prior Publication Data

US 2008/0228319 A1   Sep. 18, 2008

(51) Int. Cl.
*G06F 19/00* (2006.01)

(52) U.S. Cl. .................. 700/245; 700/249; 318/568.13; 318/568.15; 318/568.18; 318/568.2; 901/5; 901/7; 901/9

(58) Field of Classification Search ................. 700/245, 700/249; 318/568.13, 568.15, 568.18, 568.2; 901/5, 7, 9
See application file for complete search history.

(56) References Cited

U.S. PATENT DOCUMENTS

| 4,794,085 | A | | 12/1988 | Jessop et al. | |
|---|---|---|---|---|---|
| 4,837,734 | A | * | 6/1989 | Ichikawa et al. | ............ 700/249 |

(Continued)

OTHER PUBLICATIONS

Lange et al., Learning accurate path control of industrial robots with joint elasticity, 1999, IEEE, p. 2084-2089.*

(Continued)

*Primary Examiner*—Khoi H. Tran
*Assistant Examiner*—McDieunel Marc
(74) *Attorney, Agent, or Firm*—Todd J. Burns

(57) ABSTRACT

A method for aligning the position of a movable arm includes: providing an alignment element on the apparatus projecting a distance above the apparatus in the z-direction and having a surface lying in a plane formed by an x and y axis; providing a movable arm having a tool at the free end; positioning the object such that the surface of the element faces the tool; moving the tool in a direction towards the surface of the element; sensing when the tool reaches a predetermined point on or above the surface of the element, whereby the position of the tool in the z-direction is determined based on the relationship between the measured response of the tool and the height of the tool above the surface of the alignment element; placing the tool on or at a distance in the z-direction from the surface; moving the tool in the x-direction while sensing the surface of the element; moving the tool in the x-direction until an edge of the element is sensed; determining the center in the x-direction based on the known distance the tool has moved and the known dimensions of the element in the x-direction; placing the tool on or at a distance in the z-direction from the surface; moving the tool in the y-direction while sensing the surface of the element; moving the tool in the y-direction until an edge of the element is sensed; determining the center in the y-direction based on the known distance the tool has moved and the known dimensions of the element in the y-direction. In a preferred embodiment, the tool is a metering probe having a disposable tip on the end thereof. In another preferred embodiment, the measured response is the air pressure in the probe and the metering probe has a source of compressed air for expelling air out of the end of the probe and a pressure transducer for measuring the air pressure inside the metering probe.

39 Claims, 8 Drawing Sheets

U.S. PATENT DOCUMENTS

| | | | |
|---|---|---|---|
| 5,143,849 | A | 9/1992 | Barry et al. |
| 5,428,280 | A * | 6/1995 | Schmidt et al. ........ 318/568.11 |
| 5,665,601 | A | 9/1997 | Kilmer |
| 5,672,044 | A * | 9/1997 | Lemelson ................ 414/744.3 |
| 5,736,403 | A | 4/1998 | Riall et al. |
| 5,753,512 | A | 5/1998 | Riall et al. |
| 6,123,779 | A | 9/2000 | Conrad et al. |
| 6,376,265 | B1 | 4/2002 | Wong |
| 6,937,955 | B2 | 8/2005 | Barnes |
| 7,179,346 | B2 * | 2/2007 | Lam et al. .................... 156/299 |
| 7,313,462 | B2 * | 12/2007 | Woodruff et al. ........... 700/245 |
| 2003/0026733 | A1 | 2/2003 | LaCourt et al. |
| 2003/0187600 | A1 | 10/2003 | Barnes |

OTHER PUBLICATIONS

Schaufler et al., A simplified criterion for repeatability and its application in constraint path planning problems, 2000, IEEE, p. 2345-2350.*

* cited by examiner

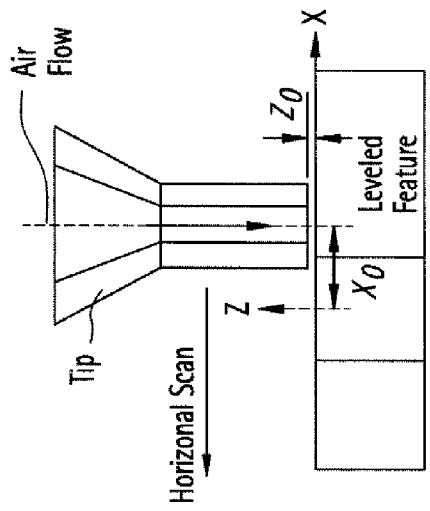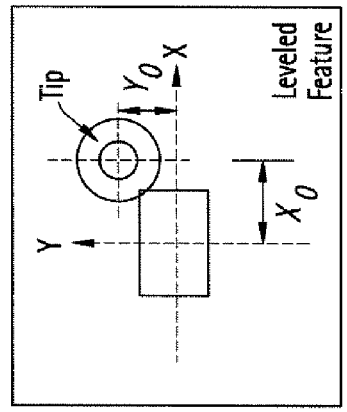
FIG. 8A    FIG. 8B
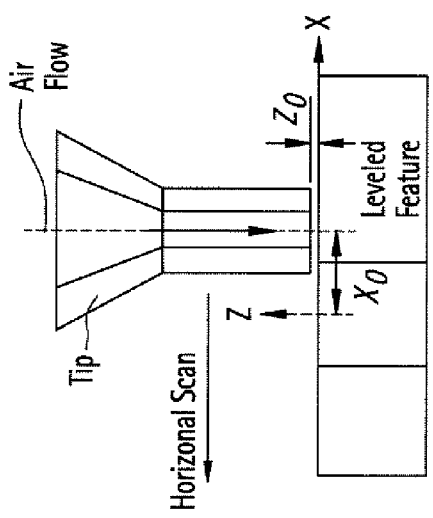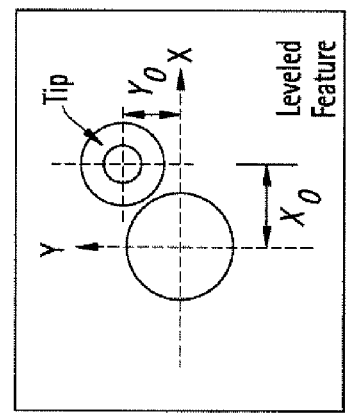
FIG. 9A    FIG. 9B

ROBOTIC ARM ALIGNMENT

BACKGROUND OF THE INVENTION

The present invention relates to automatically aligning a robotic arm, particularly in three dimensions. In particular, the present invention relates to aligning a metering arm in automated diagnostic analyzers.

Known diagnostic analyzers include immunodiagnostic analyzers such as the Vitros® ECi immunodiagnostic analyzer, or clinical chemistry analyzers such as the Vitros® 5,1 FS, both sold by Ortho-Clinical Diagnostics, Inc. All such analyzers are collectively called automated diagnostic analyzers.

Representative systems are disclosed, for example, in U.S. Published Patent Application No. 2003/0026733 and in U.S. Provisional Application No. 60/832,045 filed Jul. 20, 2006, both of which are incorporated herein by reference in their entireties. Such systems have liquid handling systems, for aspirating/dispensing a liquid such as sample or reagent. Such systems typically include a metering probe for dispensing/aspirating a liquid located on the end of a movable metering arm.

For example, as disclosed in the '045 application, the metering system includes one and sometimes two robotic arms that have the capability to move not only linearly but also rotate in a plane that is horizontal and parallel to the line of linear motion in addition to being able to move in a vertical (z-direction) to enable sample acquisition or expulsion or as well as reagent acquisition or expulsion. The robotic arms and metering heads are required to be able to position to discrete points within a reachable space, but they are physically capable of positioning anywhere within that space. Nothing physically limits the arm from reaching only a discrete touch point. A typical metering system(s) include four major elements as follows:

(1) A linear track or guide rail where the position of a truck containing a specific robotic arm on the track is controlled by its own servo or stepper motor or means for moving the arm in a forward or backward linear fashion.

(2) Robotic arm(s) capable of movement via the truck along the linear track and capable of pivoting at any point on the linear track in a plane that is horizontal and parallel to the linear track.

(3) A means, such as a metering head for sample acquisition and expulsion or reagent acquisition and expulsion attached to the end of each robotic arm.

(4) A means for vertical (z-direction) movement of the sample or reagent handling means at the ends of the robotic arms.

In one embodiment as shown in the figures, a diagnostic analyzer includes both a dry system A and a wet system B. A guide rail 2 is positioned along at least a part of the length of the analyzer. The embodiment of FIG. 1 shows both a metering system for the dry system and a metering system for the wet system. Common features of the metering system for the wet system are depicted using the same reference numeral as the dry system, except with the addition of a prime ('). The metering system includes truck 1 that moves along the guide rail 2. Pivotably attached through axis (C) (FIG. 3) to truck 1 is robotic arm 3. As FIG. 1 depicts, the robotic arm 1 is pivotable and moves through plane 4. Attached to robotic arm 1 is metering head 5. FIG. 3 shows metering head 5 in more detail. Metering head 5 includes a probe 6 also called a proboscis. The probe may include a disposable tip or may be non-disposable washable probe. As described above, the probe is movable in the vertical direction to access sample and/or reagent.

FIG. 4 shows the robotic arm 3 and metering head 5 accessing multiple (in this embodiment four) rotatable sample trays 20 having sample tubes 21 (in this embodiment ten sample tubes). As FIG. 4 depicts, the metering system is able to access the sample tubes in more than a single dimension (i.e., along the length of the guide rail). That is, the metering system by virtue of the pivotable robotic arm is able to move in an x, y, and z direction and thus able to access all areas of all of the sample trays 20.

The alignment of such metering arms on automated diagnostic analyzers needs to be verified and/or re-aligned at specified intervals to insure the performance of the metering system. Currently the alignment is performed manually by manufacturing or service personnel, which is time consuming and subject to human errors. It would be very desirable to automate this metering arm alignment procedure so that trained personnel are not needed and any operator could initiate the alignment process.

U.S. Pat. No. 6,937,955 discloses calibrating a metering arm on a clinical analyzer, which is incorporated herein by reference in its entirety.

For the foregoing reasons, there is a need for a method of automatically aligning a robotic arm to obviate the need to have manufacturing or service operator do the same.

SUMMARY OF THE INVENTION

The present invention is directed to a method that solves the foregoing problem not being able to automatically align a robotic arm without intervention by personnel.

One aspect of the invention is directed to a method for aligning the position of a movable arm. The method includes: providing an alignment element on the apparatus projecting a distance above the apparatus in the z-direction and having a surface lying in a plane formed by an x and y axis; providing a movable arm having a tool at the free end; positioning the object such that the surface of the element faces the tool; moving the tool in a direction towards the surface of the element; sensing when the tool reaches a predetermined point on or above the surface of the element, whereby the position of the tool in the z-direction is determined based on the relationship between the measured response of the tool and the height of the tool above the surface of the alignment element; placing the tool on or at a distance in the z-direction from the surface; moving the tool in the x-direction while sensing the surface of the element; moving the tool in the x-direction until an edge of the element is sensed; determining the center in the x-direction based on the known distance the tool has moved and the known dimensions of the element in the x-direction; placing the tool on or at a distance in the z-direction from the surface; moving the tool in the y-direction while sensing the surface of the element; moving the tool in the y-direction until an edge of the element is sensed; determining the center in the y-direction based on the known distance the tool has moved and the known dimensions of the element in the y-direction.

According to another aspect of the invention, there has been provided a method for aligning the position of a movable arm. The method includes: providing an alignment element on the apparatus projecting a distance above the apparatus in the z-direction and having a surface lying in a plane formed by an x and y axis, wherein the dimensions of the element in the y and z directions are known; providing a movable arm having a tool at the free end; positioning the object such that the surface of the element faces the tool; moving the tool in a direction towards surface of the element; sensing when the tool reaches a predetermined point on or above the surface of the element, whereby the position of the tool in the z-direction is determined based on the monotonic relationship between the measured response of the tool and the height of the tool above the surface of the alignment element; placing the tool on or at a distance in the z-direction from the surface; moving the tool in a positive x-direction while sensing the surface of the element until an edge of the element is sensed; moving the tool in a negative x-direction while sensing the surface of the element until the other edge of the element is sensed; determining the center of the element along the x-axis using the edges sensed by the tool in the positive and negative x-directions; placing the tool on or at a distance in the z-direction from the surface; moving the tool in a positive y-direction while sensing the surface of the element until an edge of the element is sensed; moving the tool in a negative y-direction while sensing the surface of the element until the other edge of the element is sensed; determine the center of the element along the y-axis using the edges sensed by the tool in the positive and negative y-directions; and determining the center of the element based on the known centers along the x and y-axis.

According to yet another aspect of the invention, there has been provided, a method for aligning the position of a movable arm. The method includes: providing an alignment element on the apparatus projecting a distance above the apparatus in the z-direction and having a surface lying in the plane formed by an x and y axis, and a recess in the surface, said recess extending in the z-direction; providing a movable arm having a tool at the free end; positioning the object such that the surface of the element faces the tool; moving the tool in a direction towards surface of the element; sensing when the tool reaches a predetermined point on or above the element, whereby the position of the tool in the z-direction is determined based on the relationship between the measured response of the tool and the height of the tool above a flat surface of the alignment element; placing the tool on or at a known distance in the z-direction from the surface; moving the tool in the x-direction toward the recess while sensing the surface of the element; moving the tool in the x-direction until a first edge of the recess is sensed and continuing to move the tool until a second edge of the recess is sensed; determining the center of the recess in the x-direction based on the sensed edges; placing the tool on or a at a distance in the z-direction from the surface; moving the tool in the y-direction until a first edge of the recess is sensed and continuing to move the tool until a second edge of the recess is sensed; and determining the center of the recess in the y-direction based on the sensed edges.

In a preferred embodiment, the tool is a metering probe having a disposable tip on the end thereof. In another preferred embodiment, the measured response is the air pressure in the probe and the metering probe has a source of compressed air for expelling air out of the end of the probe and a pressure transducer for measuring the air pressure inside the metering probe.

Further objects, features and advantages of the present invention will be apparent to those skilled in the art from detailed consideration of the preferred embodiments that follow.

BRIEF DESCRIPTION OF THE DRAWINGS

FIG. 8A shows a side view of a solid calibration element and metering tip where a circular recess is in the calibration element according to another embodiment of the invention.

FIG. 8B shows a plan view of FIG. 8A using the method according to this third embodiment to determine the alignment of the robotic arm.

FIG. 9A shows a side view of a solid calibration element and metering tip where a rectangular recess is in the calibration element according to another embodiment of the invention.

FIG. 9B shows a plan view of FIG. 9A using the method according to this third embodiment to determine the alignment of the robotic arm.

DETAILED DESCRIPTION OF PREFERRED EMBODIMENTS

Figure 1:
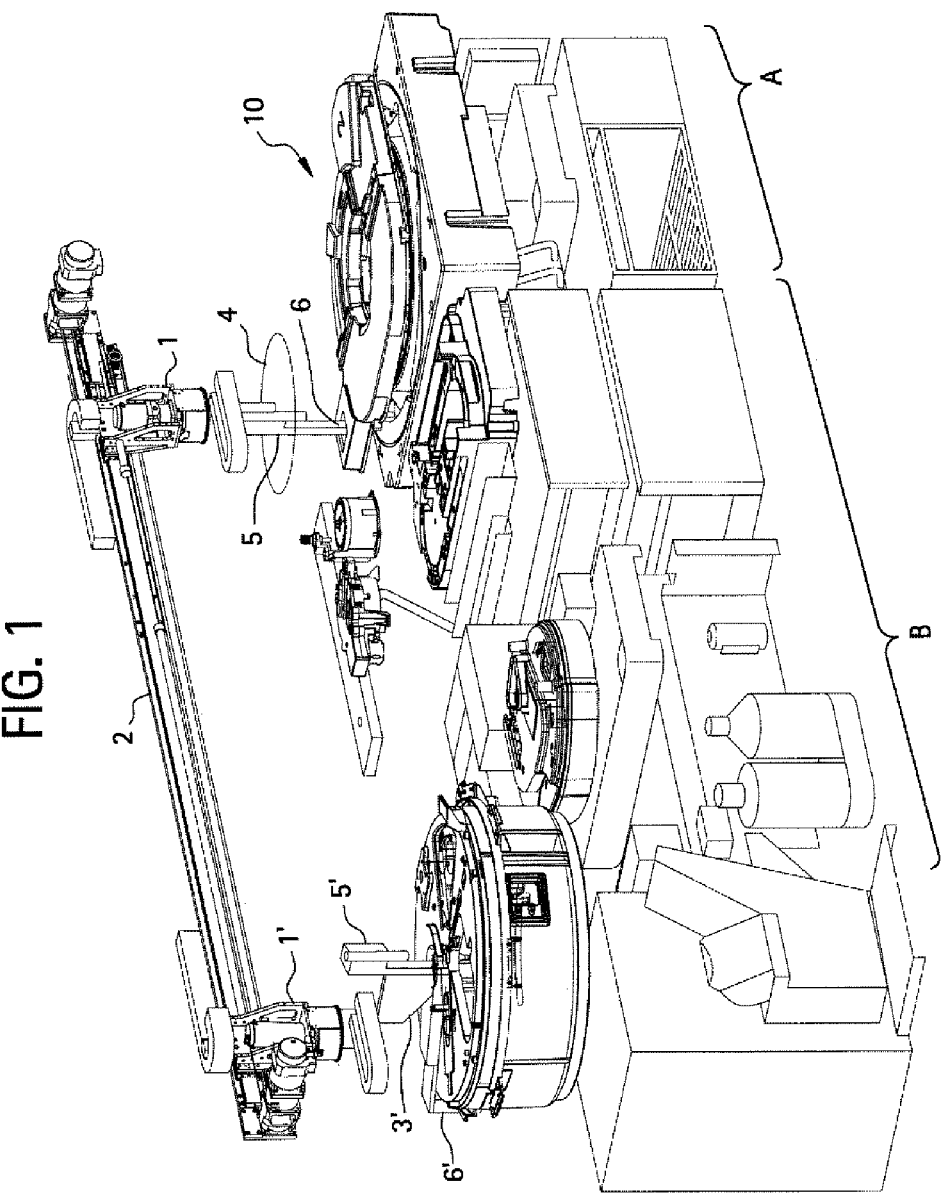
FIG. 1 is a perspective schematic view of a combinational diagnostic analyzer having two metering systems according to a preferred embodiment of the present invention.
Figure 2:
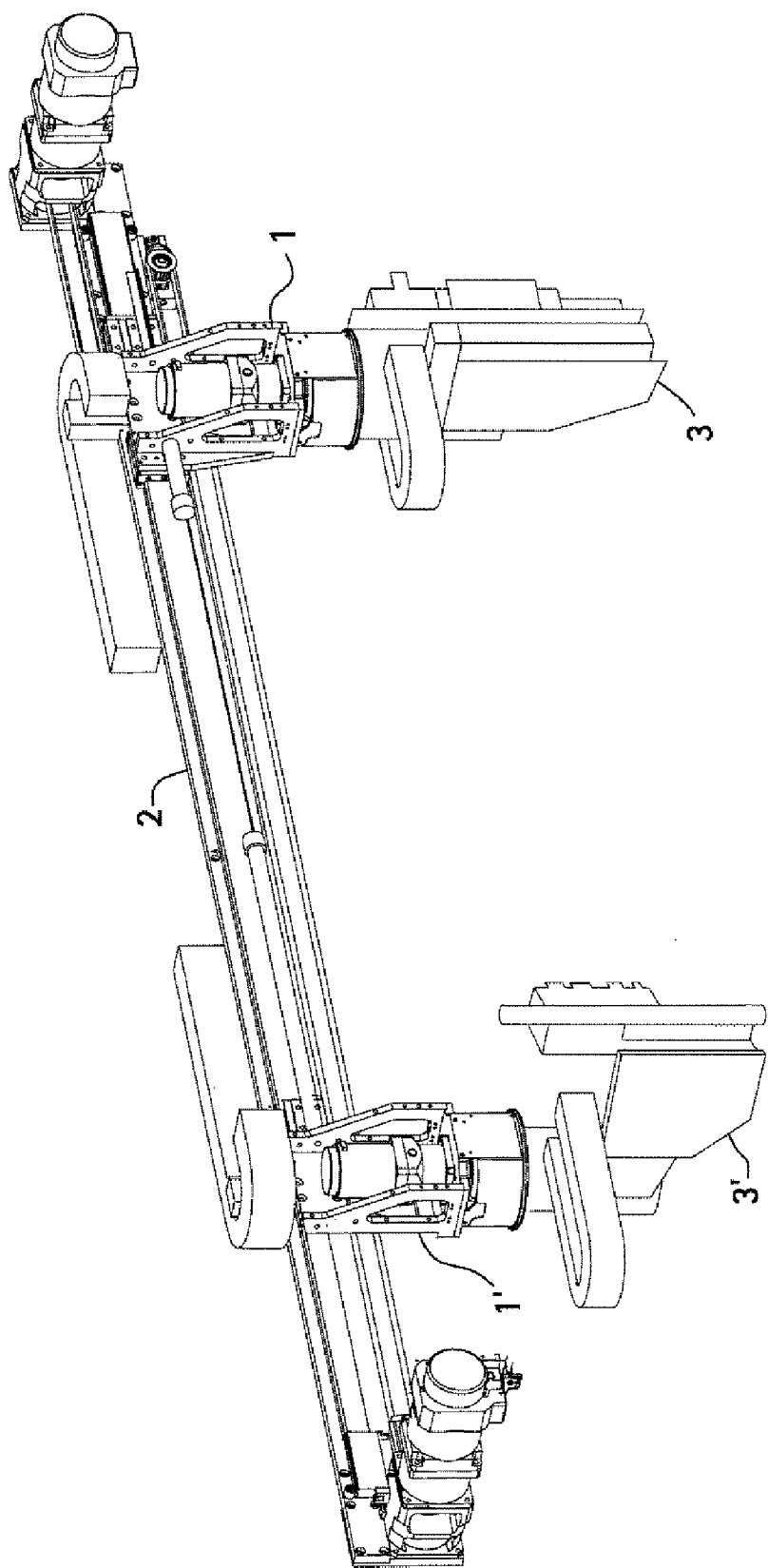
FIG. 2 is a perspective schematic view of two metering systems and the guide rail according to a preferred embodiment of the present invention.
Figure 3:
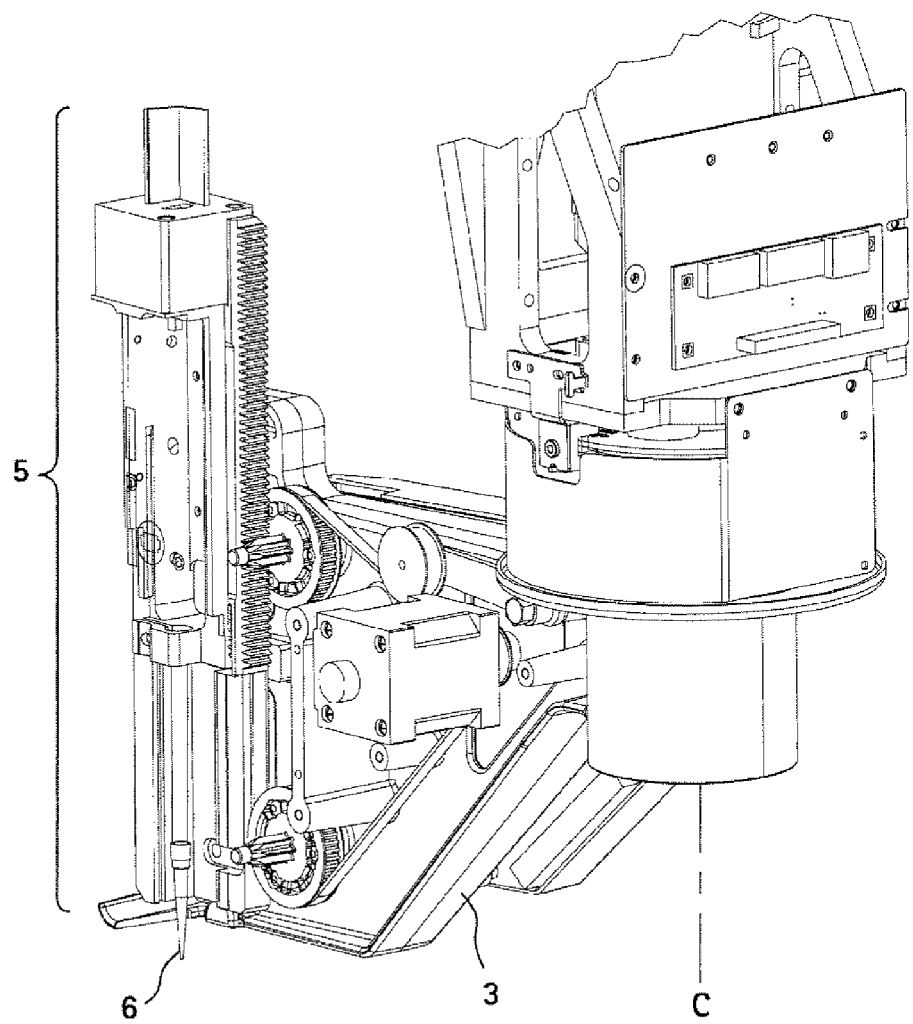
FIG. 3 is a perspective schematic view of a metering head and robotic arm pivotably attached to the rail mounted truck according to a preferred embodiment of the present invention.
Figure 4:
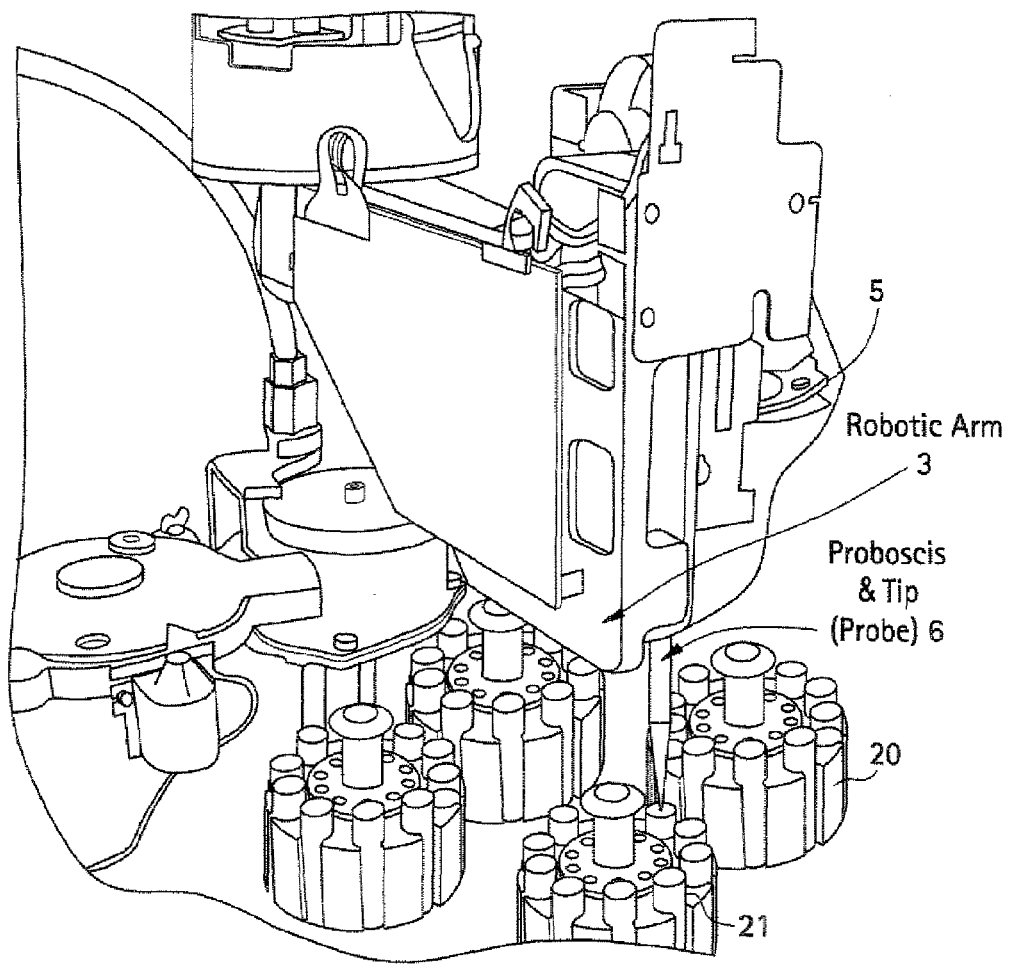
FIG. 4 shows four sample trays positioned for sample access in greater than one dimension using a robotic arm and metering head according to a preferred embodiment of the present invention.

While the present invention is described with respect to the preferred embodiment of three-dimensional alignment of a metering arm of a diagnostic analyzer having a metering probe on the end thereof, this invention is applicable to any apparatus having a robotic arm having a tool that is required to register at known three-dimensional locations. For example, a robotic arm having a welding attachment as the tool; alternatively, a robotic arm capable of moving objects within three dimensions having a gripper attachment as the tool attached thereto. Alternative uses are described below.

In a preferred embodiment, the current invention performs automatic three-dimensional alignment for the metering arm without the need for trained service personnel.

In a preferred aspect of the invention, the metering probe uses an air-based system to aspirate or dispense a liquid. The air-based metering can also be used to sense when a tip of the metering probe is approaching a solid or liquid using a well-known pressure transducer. Such systems, per se, are known and are described, for example, in U.S. Pat. Nos. 4,794,085 and 5,143,849, both incorporated herein by reference. These patents describe both blowing air out of a tip to sense surfaces by a pressure increase, and aspirating air into the tip and sensing the increase in vacuum in the probe tip as the tip approaches a surface. Other types of sensing can also be used, such as a mechanical feeler gauge, capacitive sensing, optical sensing and the like, all of which are known in the art.

Any suitable object can be used as alignment elements. One is a structure projecting a distance above the surroundings in a z-direction. A surface lying in the plane formed by an x- and y-axis may or may not have known dimensions in the x and y direction. In some embodiments, the dimensions in the x and y directions are known. In other embodiments, such dimensions do not need to be known. The x, y and z axis are preferably orthogonal to each other.

Another alignment element is similar to the one described above with a hole or recess in the surface of the element. In some embodiments, the dimensions in the x and y directions are known. In other embodiments, such dimensions do not need to be known. The x, y and z axis are preferably orthogonal to each other.

For both types of solid objects, a rectangular or square shape is preferred although other geometries, such as circular, can also be used. The alignment element can be placed, optionally removably placed, with respect to particular features on the apparatus, or alternatively, with respect to the apparatus as a whole. In the case where the feature is not placed precisely on the apparatus, placing the alignment element with respect to the feature, will allow the feature to be accessed by the robotic arm. In this case, it will be necessary that the distance or offset from the alignment element to the feature be known. Once the distance from the alignment element is know, then based on known distance, the location of the feature in relation to the alignment element will be known. As used herein, "apparatus" refers to instrumentation, such as diagnostic analyzers or high throughput screening or machines such as a milling machine or welding machine.

In a preferred aspect of the invention, there are multiple types of alignment elements. One is a solid structure with a height (z-direction) above the surrounding apparatus. Another one has a hole or recess having a depth in the alignment element. For both types of elements, a rectangular or square shape is preferred although other geometries, such as circular, can also be used. The ability to perform the adjustment for other geometries allows adjustment to actual features such as a reaction well location in a ring of a diagnostic analyzer, rather than a separate removable alignment element with a defined offset from the feature. Accordingly, in another embodiment, the alignment element is the actual feature, as opposed to a removable element. Thus, "alignment element" is defined to include an actual feature that the arm is aligned with.

A first type of alignment element is preferably a flat solid cube-shaped structure with a square surface that projects horizontally above a flat surface. The height of the projection above the flat surroundings (z-dimension) is at least 0.5 mm for more sensitive pressure detection. The width of the square (x and y-dimension) is at least 5 mm to allow the metering arm to be positioned within that range before alignment.

A second type of alignment element described more in-depth below, contains holes or recesses with depths (z-dimension) of at least 0.5 mm below a flat surface. The width of the hole or recess (x or y-dimension) is preferably at least 2 mm for better resolution. Preferably, the surface of the element that is perpendicular to the z-direction has flat features and the dimension in the z-direction is above the surrounding of the apparatus.

An alignment element that is the actual feature will, of course, have the shape of the feature, for example, a reagent well recess in the ring of diagnostic analyzer. Other examples of features can include holes in a cover of a module, etc.

Broadly, in a preferred embodiment of the invention, pressure profiles inside the tip are obtained while the piston is blowing air out of the tip and the metering probe is moving in a specified pattern above an alignment element having an approximate size and location to ensure an accurate scan of the tip across the surface of the element. The pressure profiles are then analyzed using techniques known in the art to find the height and the edge of the solid alignment element and to determine the location of the center of the solid object.

With an empty tip on the metering probe, the piston can blow air out of the tip orifice at a specified flow rate. The pressure inside the metering tip is monitored as air is blown out of the tip. As the tip orifice moves toward an element, such as a solid or liquid surface, the pressure inside the tip increases due to the increased resistance to air flow. This pressure increase is used to detect if the tip orifice is near the object surface. Since the calibration element geometry and location are fixed, the relationship between the measured air pressure in the tip and the height of the tip above a flat surface of the alignment element can be determined empirically such that for a particular air pressure the height of the tip is obtained.

In a preferred embodiment it is desirable to use a calibration element having a surface facing the metering probe that is both flat and perpendicular to the air flow for better sensitivity and to avoid contact between the tip orifice and the element. In many diagnostic analyzers the metering arm is vertical; therefore the element surface is preferably flat and horizontal. However, other orientations can be used in the present invention, such as when the metering arm is horizontal, then the surface facing the metering probe would be flat and vertical.

When starting alignment, the metering probe is positioned to the vicinity of the alignment element above the z-direction projection either automatically or by the operator with the keyboard via the adjustment dialogue, such that the arm can access the element in the x, y and z direction.

The metering arm moves from its home position toward (e.g., down toward) the surface of the element, preferably perpendicular in the z-direction while blowing air at specified rate. In the process, the pressure is monitored inside the tip. The solid surface is detected when the pressure rises above a specified threshold. The height of the metering arm from the surface of the element is determined based on the relationship between the measured air pressure in the tip and the height of the tip above a flat surface of the alignment element as described above. The distance from the home position to the surface of the element is determined based on the measured translation from the home position and the determined height above the element. Thus, the z-dimensional alignment is done.

Figure 5:
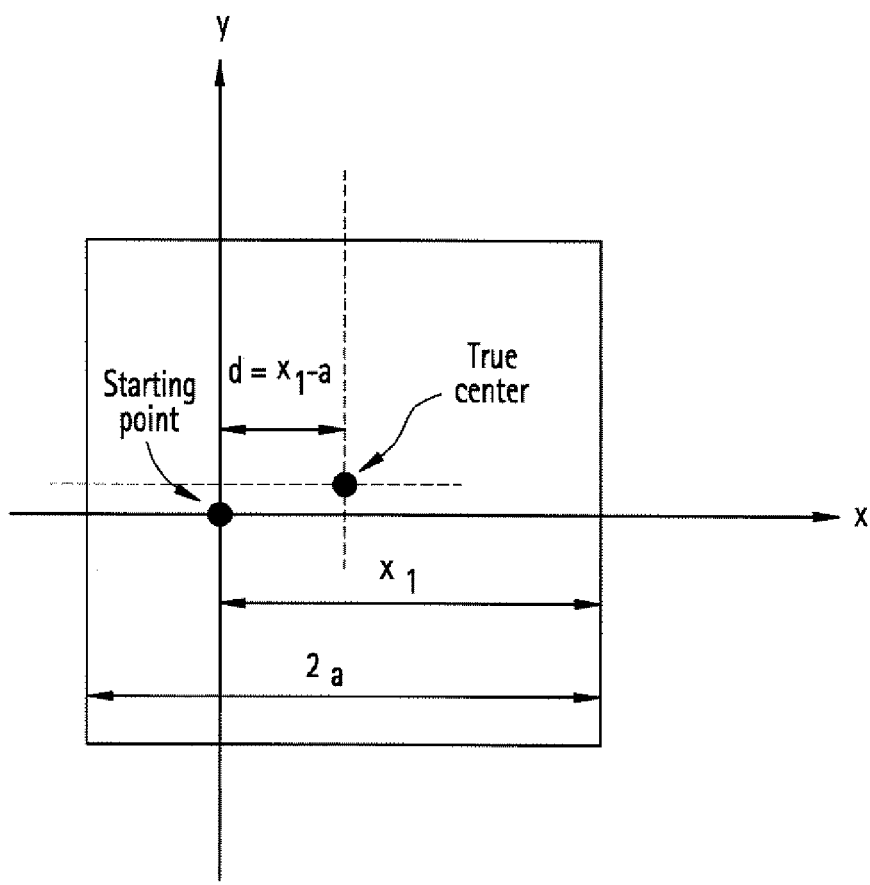
FIG. 5 shows a plan view of a calibration element showing a method for determining the position of a robotic arm according to a first embodiment of the invention.

In a first embodiment, the next step is to maintain the metering probe at a height just above the surface based on the z-direction height obtained in the previous step. In some embodiments, e.g., sensing performed via direct contact, it may be possible to maintain the metering arm in contact with the element. The metering probe is moved in the x-direction while blowing air in the process. The pressure signature is recorded and analyzed. When a pressure drop is detected in the process, the edge of the element is found in the x-direction. Based on the known size of the cubic ($2a$ as shown in FIG. 5), the center of the cubic along the x-axis can be calculated ($d=x_1-a$ as shown in FIG. 5). FIG. 5 shows the geometry and axes.

The next step is to move the metering probe in the y-direction. Preferably, the metering probe is moved to the center of the x-direction. The metering probe is then moved along the y-direction, blowing air in the process and recording the pressure signature. The center of the element in the y-direction is determined in the same fashion as the x-direction. Automated alignment in all axes (x, y, and z) is complete. As shown in FIG. 5, the center in x-direction is determined by using the length of the square surface (a) after the edge is found. Similarly the center in y-direction is determined. Alignment in either the x or y direction may be performed first.

In a second embodiment, the dimensions of the alignment element in the x and y directions need not be known beforehand. In a manner similar to previous embodiment, the metering probe tip finds the z-location of the alignment element first. The tip is then maintained on the surface or preferably just above the surface and the metering probe moves along both positive (+) x and negative (−) x axis directions while sensing the surface to find both edges in x-dimension. The center of the two edges is then calculated to determine the center at the x-axis of the alignment element. A similar process is applied for y-dimension. When determining the center for the y-direction, the probe tip may be positioned anywhere along the x-direction of the element, preferably the center in the x-direction of the element. This process may increase the time required for alignment as compared to other embodiments, but the precision should be better. As above, alignment in either the x or y direction may be performed first.

Figure 6A:
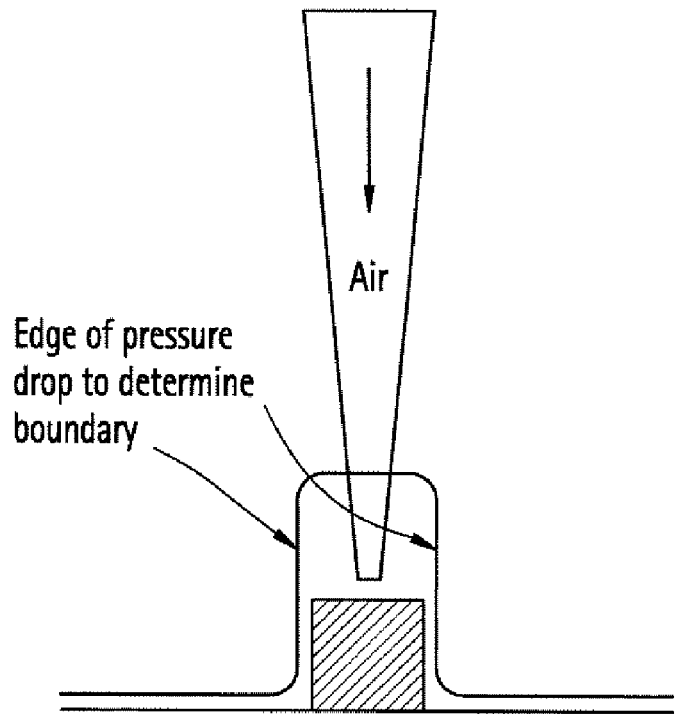
FIG. 6A shows a side view of a calibration element along with the tip of a metering probe according to a second embodiment of the invention.
Figure 6B:
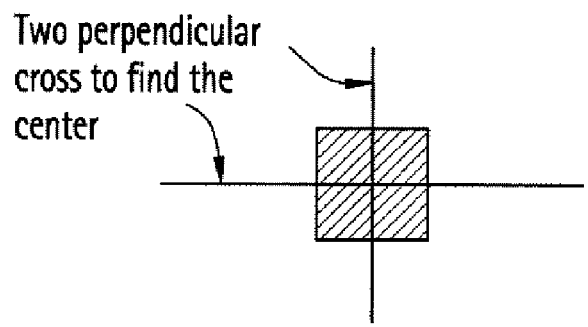
FIG. 6B shows a plan view of the calibration element shown in FIG. 6A.

FIG. 6A shows where the edge of the pressure drop is located to determine the boundaries of the element. Once the center in the x or y direction is determined, the process described above is repeated for the other direction resulting in the center of the element as shown in FIG. 6B.

Figure 7:
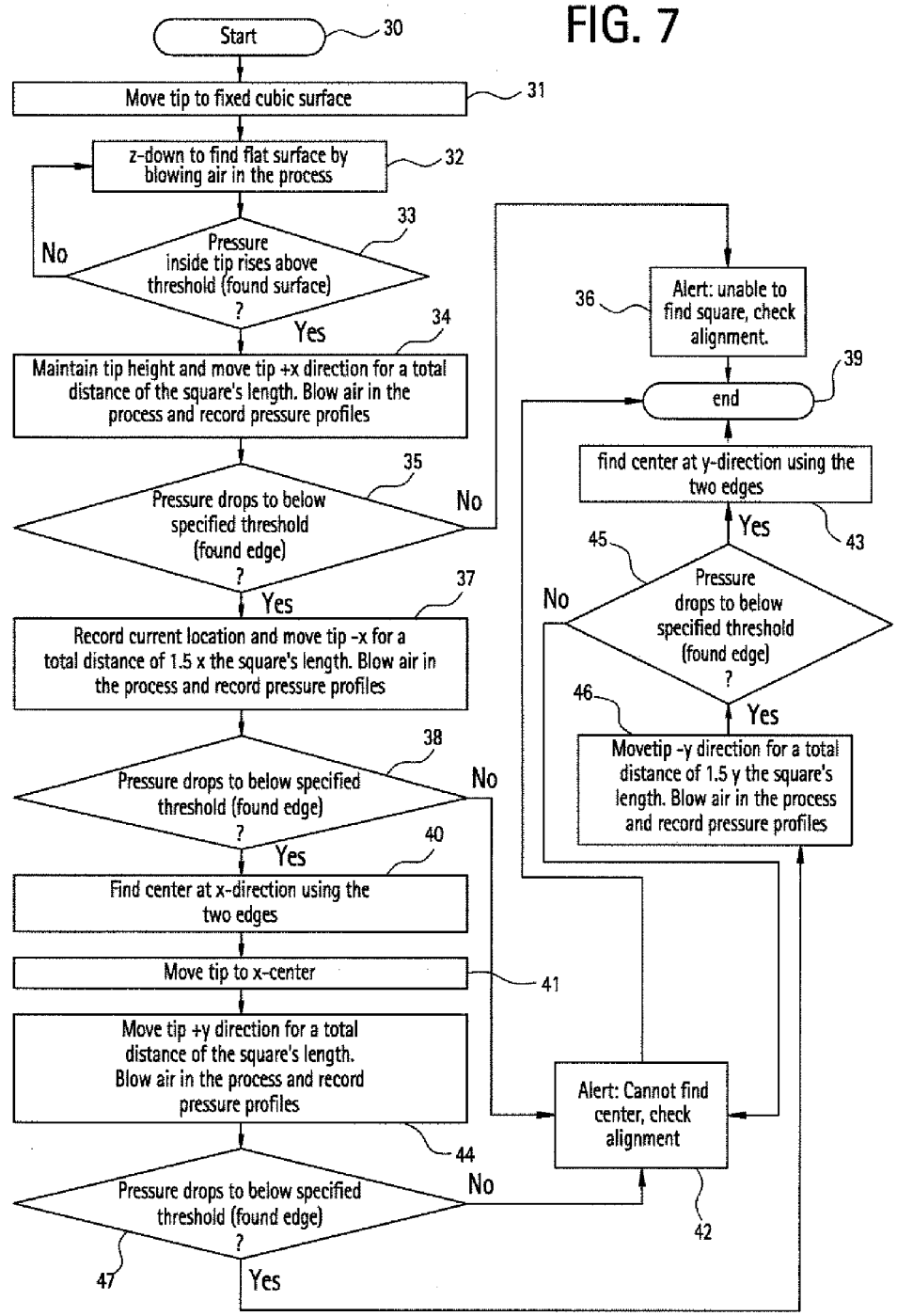
FIG. 7 shows a flowchart for an algorithm for determining the position of a robotic arm according to the embodiment of FIGS. 6A and 6B.

FIG. 7 shows a flowchart for a particularly preferred embodiment. In the FIG. 7 flowchart, the tip is first moved in the positive x and y direction for a total distance of the square's (i.e., alignment element's) length. In the movement in the negative x and y direction, the probe tip is moved 1.5 times the square's length. While specific dimensions of the element are not required, approximate dimensions are preferred. The references numerals in FIG. 7 correspond to the following text.

30—Start.
31—Move tip to fixed cubic surface.
32—Z-down to find flat surface by blowing air in the process.
33—Pressure inside tip rises to above threshold (found surface)?
34—Maintain tip height and move tip +x direction for a total distance of the square's length. Blow air in the process and record pressure profiles.
35—Pressure drops to below specified threshold (found edge)?
36—Alert: unable to find square, check alignment.
37—Record current location and move tip −x direction for a total distance of 1.5x the square's length. Blow air in the process and record pressure profiles.
38—Pressure drops to below specified threshold (found edge)?
39—End.
40—Find center at x-direction using the two edges.
41—Move tip to center.
42—Alert: cannot find center, check alignment.
43—Find center at y-direction using the two edges.
44—Move tip +y direction for a total distance of the square's length. Blow air in the process and record pressure profiles.
45—Pressure drops to below specified threshold (found edge)?
46—Move tip −y direction for total of 1.5y the square's length. Blow air in the process and record pressure profiles.
47—Pressure drops to below specified threshold (found edge)?

In yet another embodiment, a recess is located in the surface of the alignment element that is perpendicular to the z direction. The recess is preferably circular or rectangular with any dimensions. As shown in FIGS. 8A and 9A, the tip moves down to find the solid surface perpendicular to the z-direction outside the recess. In a preferred embodiment, the tip distance above the surface is determined by Z-level sensing, as described above, such that the gap size between the tip bottom and the flat surface can generate an adequate pressure signal. The tip then scans across to find the first edge of the recess or depression. When the tip encounters the recess, the pressure decreases. The tip continues scanning until the pressure spikes high again, indicating the far edge has been found. The center of the recess in the x-direction is then determined based on the distance between the two edges. When determining the center for the y-direction, the probe tip may be positioned anywhere along the x-direction of the element, preferably the center of the recess in the x-direction of the element. If the tip is located within the recess along the x-direction, it will be necessary to move the tip in both a positive (+) y direction and a negative (−) y direction to find each edge of the recess. The center of the y-axis is then determined similar to methods described for determining the center in x-axis. The center found here for both the x and y axis is the center of the recess in the solid alignment element.

As in the previous embodiments, if the x and y dimensions of the recess of the alignment element are known, the center of the recess can be calculated only from the first detected edge of the recess.

The method for automatic alignment of a robotic arm according to the present invention can be implemented by a computer program, having computer readable program code, interfacing with the computer controller of the analyzer as is known in the art.

It will be apparent to those skilled in the art that various modifications and variations can be made to the methods of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

We claim:

1. A method for aligning the position of a movable arm comprising:
   providing an alignment element on the apparatus projecting a distance above the apparatus in the z-direction and having a surface lying in a plane formed by an x and y axis;
   providing a movable arm having a tool at the free end;
   positioning the object such that the surface of the element faces the tool;
   moving the tool in a direction towards the surface of the element;
   sensing when the tool reaches a predetermined point on or above the surface of the element, whereby the position of the tool in the z-direction is determined based on the relationship between the measured response of the tool and the height of the tool above the surface of the alignment element;
   placing the tool on or at a distance in the z-direction from the surface;

moving the tool in the x-direction while sensing the surface of the element;

moving the tool in the x-direction until an edge of the element is sensed;

determining the center in the x-direction based on the known distance the tool has moved and the known dimensions of the element in the x-direction;

placing the tool on or at a distance in the z-direction from the surface;

moving the tool in the y-direction while sensing the surface of the element;

moving the tool in the y-direction until an edge of the element is sensed; and determining the center in the y-direction based on the known distance the tool has moved and the known dimensions of the element in the y-direction.

2. A method for aligning as claimed in claim 1, wherein the surface of the element is perpendicular to the tool in the z-direction.

3. A method for aligning as claimed in claim 1, wherein the tool is a metering probe.

4. A method for aligning as claimed in claim 3, wherein the metering probe has a disposable tip on the end thereof.

5. A method for aligning as claimed in claim 3, wherein the measured response is the air pressure in the probe.

6. A method for aligning as claimed in claim 3, wherein the metering probe has a source of compressed air for expelling air out of the end of the probe and a pressure transducer for measuring the air pressure inside the metering probe.

7. A method as claimed in claim 6, wherein the pressure inside the metering probe increases as the probe approaches the surface of element.

8. A method as claimed in claim 7, wherein the distance of the probe from the surface of the element is detected when the pressure reaches a predetermined threshold.

9. A method as claimed in claim 3, wherein the metering probe has one of an optical sensor, capacitive sensor, or mechanical feeler gauge.

10. A method for aligning as claimed in claim 3, wherein the metering probe has a vacuum source for drawing air into the end of the probe and a vacuum gauge for measuring the air pressure inside the metering probe.

11. A method as claimed in claim 1, wherein the apparatus is a diagnostic analyzer.

12. A method as claimed in claim 1, wherein the x, y and z directions are orthogonal to one another.

13. A method for aligning the position of a movable arm comprising:

providing an alignment element on the apparatus projecting a distance above the apparatus in the z-direction and having a surface lying in a plane formed by an x and y axis, wherein the dimensions of the element in the y and z directions are known;

providing a movable arm having a tool at the free end;

positioning the object such that the surface of the element faces the tool;

moving the tool in a direction towards surface of the element;

sensing when the tool reaches a predetermined point on or above the surface of the element, whereby the position of the tool in the z-direction is determined based on the monotonic relationship between the measured response of the tool and the height of the tool above the surface of the alignment element;

placing the tool on or at a distance in the z-direction from the surface;

moving the tool in a positive x-direction while sensing the surface of the element until an edge of the element is sensed;

moving the tool in a negative x-direction while sensing the surface of the element until the other edge of the element is sensed;

determining the center of the element along the x-axis using the edges sensed by the tool in the positive and negative x-directions;

placing the tool on or at a distance in the z-direction from the surface;

moving the tool in a positive y-direction while sensing the surface of the element until an edge of the element is sensed;

moving the tool in a negative y-direction while sensing the surface of the element until the other edge of the element is sensed;

determine the center of the element along the y-axis using the edges sensed by the tool in the positive and negative y-directions; and determining the center of the element based on the known centers along the x and y-axis.

14. A method for aligning as claim in claim 13, further comprising moving the tool to the center of the element along the x-axis after determining the center of the element along the x-axis.

15. A method for aligning as claim in claim 13, wherein the element is round.

16. A method for aligning as claimed in claim 13, wherein the surface of the element is perpendicular to the tool in the z-direction.

17. A method for aligning as claimed in claim 13, wherein the tool is a metering probe.

18. A method for aligning as claimed in claim 17, wherein the metering probe has a disposable tip on the end thereof.

19. A method for aligning as claimed in claim 17, wherein the measured response is the air pressure in the probe.

20. A method for aligning as claimed in claim 17, wherein the metering probe has a source of compressed air for expelling air out of the end of the probe and a pressure transducer for measuring the air pressure inside the metering probe.

21. A method as claimed in claim 20, wherein the pressure inside the metering probe increases as the probe approaches the surface of element.

22. A method as claimed in claim 21, wherein the distance of the probe from the surface of the element is detected when the pressure reaches a predetermined threshold.

23. A method as claimed in claim 21, wherein the x, y and z directions are orthogonal to one another.

24. A method as claimed in claim 17, wherein the metering probe has one of an optical sensor, capacitive sensor, or mechanical feeler gauge.

25. A method for aligning as claimed in claim 17, wherein the metering probe has a vacuum source for drawing air into the end of the probe and a vacuum gauge for measuring the air pressure inside the metering probe.

26. A method as claimed in claim 13, wherein the apparatus is a diagnostic analyzer.

27. A method as claimed in claim 13, wherein the x, y and z directions are orthogonal to one another.

28. A method for aligning the position of a movable arm comprising: providing an alignment element on the apparatus projecting a distance above the apparatus in the z-direction and having a surface lying in the plane formed by an x and y axis, and a recess in the surface, said recess extending in the z-direction;

providing a movable arm having a tool at the free end;
positioning the object such that the surface of the element faces the tool;
moving the tool in a direction towards surface of the element;
sensing when the tool reaches a predetermined point on or above the element, whereby the position of the tool in the z-direction is determined based on the relationship between the measured response of the tool and the height of the tool above a flat surface of the alignment element;
placing the tool on or at a known distance in the z-direction from the surface;
moving the tool in the x-direction toward the recess while sensing the surface of the element;
moving the tool in the x-direction until a first edge of the recess is sensed and continuing to move the tool until a second edge of the recess is sensed;
determining the center of the recess in the x-direction based on the sensed edges;
placing the tool on or a at a distance in the z-direction from the surface;
moving the tool in the y-direction until a first edge of the recess is sensed and continuing to move the tool until a second edge of the recess is sensed; and
determining the center of the recess in the y-direction based on the sensed edges.

29. A method for aligning as claimed in claim 28, wherein the surface of the element is perpendicular to the tool in the z-direction.

30. A method for aligning as claimed in claim 28, wherein the tool is a metering probe.

31. A method for aligning as claimed in claim 30, wherein the metering probe has a disposable tip on the end thereof.

32. A method for aligning as claimed in claim 30, wherein the measured response is the air pressure in the probe.

33. A method for aligning as claimed in claim 32, wherein the metering probe has a source of compressed air for expelling air out of the end of the probe and a pressure transducer for measuring the air pressure inside the metering probe.

34. A method as claimed in claim 33, wherein the pressure inside the metering probe increases as the probe approaches the surface of element.

35. A method as claimed in claim 34, wherein the distance of the probe from the surface of the element is detected when the pressure reaches a predetermined threshold.

36. A method as claimed in claim 30, wherein the metering probe has one of an optical sensor, capacitive sensor, or mechanical feeler gauge.

37. A method for aligning as claimed in claim 30, wherein the metering probe has a vacuum source for drawing air into the end of the probe and a vacuum gauge for measuring the air pressure inside the metering probe.

38. A method as claimed in claim 28, wherein the apparatus is a diagnostic analyzer.

39. A method for calibrating as claimed in claim 28 further comprising, determining the center of the recess based on the known centers along the x and y-axis.

* * * * *